(12) United States Patent
Stepp et al.

(10) Patent No.: US 10,017,526 B2
(45) Date of Patent: Jul. 10, 2018

(54) METHOD FOR PRODUCING SILOXANES FROM ALKALI SALTS OF SILANOLS

(71) Applicant: Wacker Chemie AG, Munich (DE)

(72) Inventors: Michael Stepp, Ueberackern (AT); Herbert Koller, Emmerting (DE)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 15/322,775

(22) PCT Filed: Jun. 29, 2015

(86) PCT No.: PCT/EP2015/064719
§ 371 (c)(1),
(2) Date: Dec. 29, 2016

(87) PCT Pub. No.: WO2016/001154
PCT Pub. Date: Jan. 7, 2016

(65) Prior Publication Data
US 2017/0166595 A1    Jun. 15, 2017

(30) Foreign Application Priority Data

Jul. 1, 2014  (DE) .................. 10 2014 212 698

(51) Int. Cl.
*C07F 7/21* (2006.01)

(52) U.S. Cl.
CPC .................................... *C07F 7/21* (2013.01)

(58) Field of Classification Search
CPC ................ C08F 290/148; C08F 230/08; C08F 2220/301
See application file for complete search history.

(56) References Cited

U.S. PATENT DOCUMENTS

| | | |
|---|---|---|
| 2,567,110 A | 9/1951 | Hyde |
| 2005/0009982 A1 | 1/2005 | Inagaki et al. |
| 2005/0038220 A1 | 2/2005 | Shin et al. |
| 2005/0250925 A1* | 11/2005 | Oikawa ............... C07F 7/21 528/25 |
| 2013/0145966 A1 | 6/2013 | Schildbach et al. |
| 2014/0228589 A1 | 8/2014 | Stepp et al. |
| 2014/0296556 A1 | 10/2014 | Stepp et al. |

FOREIGN PATENT DOCUMENTS

| | | |
|---|---|---|
| DE | 60 2004 010 461 T2 | 11/2008 |
| EP | 1 548 020 A1 | 6/2005 |
| EP | 1 550 664 A1 | 7/2005 |
| JP | 2013241497 A | 12/2013 |
| WO | 2012/022544 A1 | 2/2012 |
| WO | 2013/041385 A1 | 3/2013 |
| WO | 2013/075969 A1 | 5/2013 |

OTHER PUBLICATIONS

Laine et al., Synthesis, functionalization and properties of incompletely condensed "half cube" silsesquioxanes as a potential route to nanoscale Janus particles, Elsevier, Scient Direct, C.R. Chimie 13 (2010) pp. 270-281.
Pozdniakova et al., "Alkali-Metal-Directed Hydrolytic Condensation of Trifunctional Phenylalkoxysilanes", Eur. J. Inorg. Chem, 2004, pp. 1253-1261.
O.I. Shchegolikhina et al., cis-Tetra[(organo)(trimethoylsiloxy)]cyclotetrasiloxanes: synthesis and mesomorphic properties, Russian Chemical Bulletin, vol. 56, No. 1, pp. 83-90, 2007.

* cited by examiner

*Primary Examiner* — Pancham Bakshi
(74) *Attorney, Agent, or Firm* — Brooks Kushman P.C.

(57) ABSTRACT

Cyclic siloxanes are prepared economically by reaction of an alkali metal siliconate having a mol ratio of alkali metal cation to silicon of less than one or their hydrolysis/condensation products or mixture thereof, with a halosilane.

21 Claims, No Drawings

METHOD FOR PRODUCING SILOXANES FROM ALKALI SALTS OF SILANOLS

CROSS REFERENCE TO RELATED APPLICATIONS

This application is the U.S. National Phase of PCT Appln. No. PCT/EP2015/064719 filed Jun. 29, 2015, which claims priority to German Application No. 10 2014 212 698.3 filed Jul. 1, 2014, the disclosures of which are incorporated in their entirety by reference herein.

BACKGROUND OF THE INVENTION

1. Field of the Invention

The invention relates to a process for preparing siloxanes from alkali metal salts of organosilanols (also referred to hereinafter as siliconates) wherein the molar ratio of alkali metal cation to silicon is <1 with halosilanes.

2. Description of the Related Art

Defined cyclic siloxanes of the general formula (1)

$$[RSi(OSiR^1R^2R^3)O]_n \tag{1}$$

are of great industrial interest as, for instance, highly reactive crosslinkers for optical, electronic, and high-temperature applications, as thermally stable solvents, as complexing agents, as fluids for cosmetic applications, and as potential building blocks for siloxane polymers. To date they have been very costly and inconvenient to produce, thus making their production uneconomical and unsuited to production on an industrial scale.

U.S. Pat. No. 2,567,110 (Corning Glass, 1947) describes very generally a process for preparing organosiloxanes by reaction of alkali metal salts of organosilanols with chlorosilanes. In the description there are indeed cyclic structures for salts of organosilanols (RSiOOAlkali)$_n$, but there are no cyclic siloxanes of the structure (RSiOSiR'$_3$O)$_n$ derivable therefrom. In the salts of the mono-organosilanols, the alkali:Si ratio is 1, 2 or 3 in each case. In the sole examples with monoorganosilanol salts (ex. 1: sodium methylsiliconate, ex. 2 sodium phenylsiliconate), the reactions with trimethylchlorosilane in a solvent mixture lead in each case to high molecular mass polysiloxanes.

JP 2013-241497 (Nat. Univ. Corp. Gunma Univ., 2012) describes the preparation of sodium or potassium siliconates starting from C$_2$-C$_8$ trialkoxysilanes and sodium hydroxide or potassium hydroxide solution in a solvent. Solid products are obtained by filtration and drying of the filter cake. The alkali:Si ratio here is 1:1. These siliconates are reacted subsequently with chlorosilanes (e.g., HM2-silane) in the presence of solvents and pyridine to give the corresponding cyclosiloxanes (e.g., [MeSi(OSiMe$_2$H)O]$_4$).

According to Shchegolikhina, O. I. et al., European Journal of Inorganic Chemistry, 2004, 1253-1261, cyclic sodium and potassium phenylsiloxanolates are prepared from phenyltriethoxysilane with aqueous sodium or potassium hydroxide solution, optionally in the presence of alcohols and organic nonpolar solvents. The alkali/Si ratio in each case is 1:1. The reaction products are reacted in the presence of pyridine with trimethylchlorosilane to give the corresponding cyclic derivatives (cis-[PhSi(OSiMe$_3$)O]$_4$ or $_3$).

Shchegolikhina, O. I. et al., Russian Chemical Bulletin, International Edition, Vol. 56, No. 1, pp. 83-90, January 2007, describes siliconate salts having an alkali:Si ratio of 1:1 as starting materials for the target compounds. They are converted into corresponding cyclic siloxanes using a large excess (>8 eq. relative to siliconate) of trimethylchlorosilane in the presence of pyridine as a base in high dilution in hexane as solvent. The alcohol bound in the crystal, and any additional water from the preparation of the siliconate, consumes a part of the chlorosilane, thus reducing the economics of the operation.

According to Laine, R. M et al., Comptes Rendus Chimie 13, 270-281, 2010, octaphenylsilsesquioxane, for example, is cleaved to give the corresponding cyclic sodium siloxanolate within 24-48 h using an excess of NaOH in butanol. The siloxanolate is reacted with methyltrichlorosilane in methanol to give a dimethoxysilyl derivative, which can be subjected to hydrolysis/condensation to form an asymmetrical silsesquioxane ("Janus silsesquioxane cube").

DE 602004010461 T2 (Samsung Electronics Co., 2004) includes in its description polyfunctional cyclic siloxane compounds such as, for example, [MeSiO(SiMe$_2$Cl)O]$_4$ and [MeSiO(SiMe$_2$-OMe)O]$_4$.

In accordance with the prior art cited above, cyclic products of the general formula (1)

$$[RSi(OSiR^1R^2R^3)O]_n \tag{1}$$

are accessible from the corresponding alkali metal siliconates of the general formula (2a)

$$RSi(OH)_2OM \tag{2a}$$

where M is an alkali metal, R is an organic radical, and n is 3, 4, 5, 6, 7 or 8, or from their condensation products, by reaction with halosilanes of the general formula (3)

$$R^1R^2R^3Si\text{-Hal} \tag{3}$$

where Hal is a halogen radical and R$^1$, R$^2$, and R$^3$ independently of one another are a hydrogen radical, a halogen radical or an organic radical optionally bonded via oxygen. The alkali:silicon ratio (M:Si) here in the general formula (2a) is always 1:1.

These siliconates are obtained by reaction either of one mole equivalent of alkoxysilane of the general formula (4)

$$RSi(OR')_3 \tag{4}$$

or its hydrolysate with one mole equivalent of aqueous alkali metal hydroxide. R has the definition above and R' in formula (4) is a lower alkyl radical.

As a result of the high alkali metal content of the siliconate, complete conversion to the target product of the general formula (1) produces one mole equivalent of alkali metal salt per mole equivalent of siliconate, the salt having to be recycled or disposed of, which is expensive. A further disadvantage arising from the high alkali metal content is the hygroscopicity of salts, which increases with rising alkali metal content, and which means that the siliconates used according to the prior art are difficult to free from alcohol or water of hydration that is bound in the crystal or is adhering (see Shchegolikhina, O. I. et al., European Journal of Inorganic Chemistry, 2004, 1253-1261). For economic reasons, however, it is necessary to employ a water-free and alcohol-free siliconate in the reaction with the halosilane of the general formula (3), since otherwise a portion of the halosilane is consumed for the reaction with the OH-functional secondary constituents, and is not available for the desired reaction with the siliconate. If drying is not carried out completely, it is necessary, for maximum conversion of the water-moist and alcohol-moist siliconate into the target product of the general formula (1), to use an excess of halosilane of the general formula (3), but this is uneconomical, because it leads to unwanted secondary products which require disposal. Another aspect is the decomposition tendency of the siliconates, which likewise shifts toward lower temperatures as the alkali metal content goes up, with a prolongation of the drying times (cf. WO2012/022544). The processes described to date in the technical literature for preparing the siloxanes of the general formula (1) according to the invention, by reaction of the dried siliconates of the general formula (2a) with halosilanes of the general formula (3), always use a solvent. After the reaction, however, these solvents have to be removed again, in a costly and inconvenient procedure, from the target products of the general formula (1).

SUMMARY OF THE INVENTION

It was an object of the invention, therefore, to provide a process for preparing compounds of the general formula (1) that does not have the disadvantages described for the prior art. A subject of the invention is a process for preparing cyclic siloxanes of the general formula (1)

[RSi(OSiR$^1$R$^2$R$^3$)O]$_n$     (1)

by reaction of alkali metal salts of silanols (known as alkali metal siliconates) consisting of units of the general formula (2)

R—Si(OH)$_{3-m}$(OM)$_m$     (2), of their hydrolysis/condensation products, or of alkali metal salts of silanols of the general formula (2) together with their condensation products, wherein the molar ratio of cation M to silicon is <1,
with halosilanes of the general formula (3)

R$^1$R$^2$R$^3$Si-Hal     (3)

where
m is 0, 1, 2 or 3 and on average is a number from 0.1 to <1,
n is 3, 4, 5, 6, 7 or 8,
R is an organic radical bonded via carbon,
M is an alkali metal cation,
Hal is a halogen radical, and
R$^1$, R$^2$, and R$^3$ independently of one another are a hydrogen radical, a halogen radical or an organic radical bonded to silicon via carbon or via oxygen.

Surprisingly, it has been found that alkali metal siliconates of the general formula (2) or condensation products thereof for which the alkali metal:silicon ratio is <1, in the reaction with halosilanes of the general formula (3), produce comparable yields of cyclic siloxanes of the general formula (1) as those with an equimolar ratio. It has also been found that in the case of the alkali metal siliconates produced according to WO2012/022544, at alkali metal:silicon ratios <1, the fractions of cyclic siloxane structures of the general formula (1) that are formed are in fact higher than in the equimolar case (see examples 1).

DETAILED DESCRIPTION OF THE PREFERRED EMBODIMENTS

The advantages of the process of the invention come about as a result of a lower alkali metal content in the siliconate of the general formula (2). These lower-alkali siliconates can be dried more easily and more reliably. Moreover, they bind less water and alcohol and therefore do not consume additional quantities of halosilane of the general formula (3).

The alkali metal salts of silanols used in the process, consisting of units of the general formula (2), and their condensation products, are referred to hereinafter collectively as siliconates A.

The radical R is preferably a monovalent, Si—C-bonded hydrocarbon radical having 1 to 30 carbon atoms, which is unsubstituted or substituted by halogen atoms, C$_{1-6}$ alkyl groups, or C$_{1-6}$ alkoxy groups, or silyl groups, and in which one or more, mutually nonadjacent —CH$_2$— units may have been replaced by —O— or —S— groups. The radical R may be linear, branched, cyclic, aromatic, saturated or unsaturated.

Preferably R is a monovalent hydrocarbon radical having 1 to 18 carbon atoms which is unsubstituted or substituted by halogen atoms, alkoxy groups or silyl groups. Particularly preferred are unsubstituted alkyl radicals, cycloalkyl radicals, alkylaryl radicals, arylalkyl radicals, and phenyl radicals. The hydrocarbon radical R preferably has 1 to 6 carbon atoms. More preferred are the methyl, ethyl, propyl, 3,3,3-trifluoropropyl, vinyl, n-hexyl, and phenyl radicals, yet more preferably the methyl radical and the vinyl radical, and most preferably the methyl radical.

Further examples of radicals R are:
n-propyl, 2-propyl, chloromethyl, methoxymethyl, 3-chloropropyl, 2-(trimethylsilyl)ethyl, n-butyl, 2-butyl, 2-methylpropyl, tert-butyl, n-pentyl, cyclopentyl, n-hexyl, cyclohexyl, n-heptyl, n-octyl, 2-ethylhexyl, n-nonyl, n-decyl, n-undecyl, 10-undecenyl, n-dodecyl, isotridecyl, n-tetradecyl, n-hexadecyl, vinyl, allyl, benzyl, p-chlorophenyl, o-(phenyl)phenyl, m-(phenyl)phenyl, p-(phenyl)phenyl, 1-naphthyl, 2-naphthyl, 2-phenylethyl, 1-phenylethyl, and 3-phenylpropyl. Further examples of R are radicals —(CH$_2$O)$_o$—R$^8$, —(CH$_2$CH$_2$O)$_p$—R$^9$, and CH$_2$CH(CH$_3$)O)$_q$—R$^{10}$, where o, p and q have values from 1 to 10, more preferably 1, 2, 3. Preferably, R$^8$, R$^9$, and R$^{10}$ are alkyl radicals having 1 to 6 carbon atoms which are unsubstituted or substituted by halogen atoms. Examples of radicals R$^8$, R$^9$, and R$^{10}$ are the methyl, ethyl, propyl, allyl, and butyl radicals, the methyl radical being particularly preferred.

M is lithium, sodium, potassium or cesium, with sodium and potassium being preferred, and potassium being most preferred.

The molar ratio M:Si in the general formula (2), represented by the average value of m, is preferably at least 0.1, more preferably at least 0.4, and most preferably at least 0.5, and preferably at most 0.95, more preferably at most 0.85, and most preferably at most 0.75.

If M is sodium and potassium, the molar ratio of K:Na in the siliconate A is preferably 0.8:0.2 to 0.4:0.6, more preferably 0.7:0.3 to 0.5:0.5.

Preferably, n is 4, 5 or 6.

The siliconates of the invention are preferably prepared by the processes described in WO2013/041385, WO2012/022544, and WO2013/075969.

The radicals R$^1$, R$^2$, and R$^3$ in the halosilane of the general formula (3) are preferably the hydrogen radical or a halogen, a C$_{1-10}$ alkoxy radical, or a C$_{1-20}$ aryloxy radical, or a monovalent hydrocarbon radical having 1 to 18 carbon atoms which is unsubstituted or substituted by halogen atoms, alkoxy groups or silyl groups. Particularly preferred are hydrogen, fluoro, chloro, bromo, iodo, C$_{1-6}$ alkoxy, C$_{1-10}$ aryloxy, and unsubstituted C$_{1-10}$ alkyl radicals, C$_{1-10}$ cycloalkyl radicals, C$_{1-20}$ alkylaryl radicals, C$_{1-20}$ arylalkyl radicals, and phenyl radicals. Especially preferred are the hydrogen, methyl, ethyl, propyl, 3,3,3-trifluoropropyl, vinyl, n-hexyl, and phenyl radicals, especially the methyl radical and the vinyl radical, most preferably the methyl radical.

Further examples of radicals R$^1$, R$^2$, and R$^3$ are as follows: n-propyl, 2-propyl, chloromethyl, methoxymethyl, 3-chloropropyl, 2-(trimethylsilyl)ethyl, 2-(trimethoxysilyl)ethyl, 2-(triethoxysilyl)ethyl, 2-(dimethoxymethylsilyl)

ethyl, 2-(diethoxymethylsilyl)ethyl, n-butyl, 2-butyl, 2-methylpropyl, tert-butyl, n-pentyl, cyclopentyl, n-hexyl, cyclohexyl, n-heptyl, n-octyl, 2-ethylhexyl, n-nonyl, n-decyl, n-undecyl, 10-undecenyl, n-dodecyl, isotridecyl, n-tetradecyl, n-hexadecyl, ethynyl, allyl, benzyl, p-chlorophenyl, o-(phenyl)phenyl, m-(phenyl)phenyl, p-(phenyl)phenyl, 1-naphthyl, 2-naphthyl, 2-phenylethyl, 1-phenylethyl, and 3-phenylpropyl.

The halosilanes of the general formula (3) are preferably chlorosilanes.

Examples of chlorosilanes of the general formula (3) are $SiCl_4$, $HSiCl_3$, $MeSiCl_3$, $ViSiCl_3$, allyl-$SiCl_3$, $PhSiCl_3$, $HSiMeCl_2$, $H_2SiCl_2$, $Me_2SiCl_2$, $ViSiMeCl_2$, $PhSiMeCl_2$, $H_3SiCl$, $Me_3SiCl$, $HSiMe_2Cl$, $ViSiMe_2Cl$, $PhSiMe_2Cl$, allyl-$SiMe_2Cl$, $F_3C-CH_2CH_2-SiMe_2Cl$, $(EtO)_3SiCl$, $(MeO)_3SiCl$, $(EtO)_2SiMeCl$, $(MeO)_2SiMeCl$, $EtOSiMe_2Cl$, $MeOSiMe_2Cl$, $Cl-CH_2-SiMe_2Cl$, $Cl-CH_2-SiMeCl_2$, and $Cl-CH_2-SiCl_3$.

Particularly preferred are $Me_3SiCl$, $HSiMe_2Cl$, $ViSiMe_2Cl$, $PhSiMe_2Cl$, $Cl-CH_2-SiMe_2Cl$, and allyl-$SiMe_2Cl$, most preferably $Me_3SiCl$, $HSiMe_2Cl$, and $ViSiMe_2Cl$.

The halosilanes are preferably prepared in the methylchlorosilane synthesis according to the Müller-Rochow process, or can be prepared as follow-on products by chemical reactions in accordance with known methods (e.g., hydrosilylation, nucleophilic substitution, and radical substitution), and are usually available commercially.

The compounds of the general formula (1) are obtained in accordance with the process of the invention by reaction of the siliconates A with the halosilanes of the general formula (3). This can be done by adding the siliconate A to the halosilanes or conversely by adding the halosilane to the siliconate A.

Advantageously here at least one component is in liquid form, such as in suspension or solution, for example. Under atmospheric pressure and at room temperature, the majority of halosilanes are liquid, and the siliconates A solid. It is therefore appropriate to dissolve or suspend the siliconates A in an inert solvent and to meter the liquid halosilanes in pure form or in solution in an inert solvent, in order to ensure a very rapid reaction by virtue of thorough mixing. Solvents employed are preferably aprotic polar and apolar organic solvents, examples being linear, branched or cyclic alkanes such as n-pentane, n-hexane, n-heptane, n-octane, isohexane, isooctane, and cyclohexane; aromatics such as benzene, toluene, o-xylene, m-xylene, and p-xylene; ethers such as diethyl ether, dipropyl ether, dibutyl ether, methyl tert-butyl ether, phenyl methyl ether, diphenyl ether, tetrahydrofuran, dioxane, tetrahydropyran, 4-methyltetrahydropyran, ethylene glycol dimethyl ether, diethylene glycol dimethyl ether, triethylene glycol dimethyl ether, ethylene glycol dibutyl ether, or siloxanes, such as hexamethyldisiloxane, octamethyltrisiloxane, octamethylcyclotetrasiloxane, decamethylcyclopentasiloxane, methyltristrimethylsiloxysilane, or mixtures of different solvents.

To scavenge the hydrogen halide formed in the reaction it is possible to add an auxiliary base. Auxiliary bases which can be used are basic salts or nitrogen-containing compounds such as amines, ureas, imines, guanidines, and/or amides. Examples of basic salts are sodium carbonate, sodium hydrogencarbonate, potassium carbonate, potassium hydrogencarbonate, calcium carbonate, calcium hydrogencarbonate, calcium oxide, magnesium carbonate, and magnesium oxide. Examples of nitrogen-containing compounds are ammonia, ethylamine, butylamine, trimethylamine, triethylamine, tributylamine, urea, tetramethylurea, guanidine, tetramethylguanidine, N-methylimidazole, N-ethylimidazole, piperidine, pyridine, and picoline. Nitrogen compounds employed with preference are those wherein the nitrogen atoms do not carry a hydrogen.

The auxiliary base is used preferably in at least equimolar proportions relative to the siliconate A. For each mole equivalent of silicon in the siliconate A, preference is given to using at least 0.5, more preferably at least 1.0, more particularly at least 2.0 base equivalents of auxiliary base. While it is also possible to use greater amounts of added auxiliary base, such amounts generally do not bring any advantage, instead reducing the space/time yield and thus lowering the profitability of the process. The auxiliary base is preferably included in an initial charge with the siliconate A, and the halosilane of the general formula (3) is metered in. Alternatively, both reactants can be metered in parallel to the auxiliary base, which is included in the initial charge. Mixtures of different auxiliary bases can be used as well.

In one preferred embodiment of the process of the invention, the siliconate A is reacted directly with the halosilane of the general formula (3), without auxiliary base and without solvent. In this case, a further advantage of the process of the invention is manifested: on account of the relatively low alkali metal fraction, the siliconate A contains free SiOH groups, which evolve gaseous hydrogen halide in the reaction of the halosilane of the general formula (3). This hydrogen halide can easily be returned to production operations, for example, in a combined hydrogen chloride system, and hence inexpensively recycled. If no auxiliary base is present, the siliconate A is preferably metered into the halosilane. With preference, the hydrogen halide gas formed in this process is carried out by a stream of inert gas or removed from the reaction mixture as soon as it has formed, by means of reduced pressure, in order to prevent unwanted secondary reactions between the siliconate A and the hydrogen halide.

With preference, the halosilane of the general formula (3) is used in at least equimolar proportions relative to the siliconate A. For each mole equivalent of siliconate silicon there is preferably at least 0.5, more preferably at least 1.0, and most preferably at least 1.5 mole equivalents of halosilane of the general formula (3).

Preference is given to using not more than 30 mole equivalents, more preferably not more than 10 mole equivalents, and most preferably not more than 6 mole equivalents of halosilane per mole equivalent of siliconate A. The greater the proportion of silicon-bonded halogen in the silane of the general formula (3), the higher the selected excess of halosilane of the general formula (3), in order to prevent inter- and intra-molecular condensation reactions, which in uncontrolled form can lead to crosslinked structures.

Mixtures of different halosilanes of the general formula (3) and siliconates A can also be used. It is also possible, especially when using an auxiliary base, for the siliconate A to be reacted successively first with a substoichiometric proportion of halosilane of the general formula (3), and thereafter with a second halosilane of the general formula (3). By this route it is also possible to access siloxanes of the general formula (1) having different units $SiR^1R^2R^3$.

The reaction of siliconate A with the halosilane of the general formula (3) is preferably carried out preferably at a temperature of at least −20° C., more preferably at least 0° C., and most preferably at least 10° C. The maximum attainable temperature is additionally a product of the boiling point of the lowest-boiling component.

In order to prevent decomposition of the siliconate A, the reaction temperature preferably does not exceed 200° C., and more preferably the reaction temperatures are not more than 120° C., most preferably not more than 70° C.

In this context, the reaction mixture may both be cooled or heated, and individual components may also be brought to a particular temperature before they come into contact with one another, in order to allow the heat of reaction to be utilized, for example.

The process may be carried out either batchwise, in a stirring mechanism, for example, or continuously, in a loop or tube reactor or in a fluidized bed reactor or in a paddle dryer, for example. If the siliconate A is metered as a solid or suspension, this metering may take place via a solids lock (e.g., conveyor screw or starwheel lock).

The reaction of the siliconate A with the halosilane of the general formula (3) customarily produces mixtures of different siloxanes of the general formula (1), which may differ in ring size (index n) and/or in steric configuration. Additionally, to a minor extent, optionally, siloxane secondary products are formed which have a linearly branched structure rather than a cyclic structure. In many cases, after the salts formed during the reaction and any solvents or other auxiliaries present have been removed, these mixtures can be used directly. If, however, there is a desire for isolation or accumulation of particular species in the reaction mixture, this is preferably done by means of fractional distillation or crystallization following removal of the resultant salts from the reaction mixture.

The halide salts formed in the reaction from the alkali metal siliconate and from the optional auxiliary base may be subjected, before or after the distillation or crystallization, to removal by filtration or to dissolution in water and removal in the form of an aqueous solution. For aqueous workup, it is possible additionally to add a solvent having an extremely low solubility in water, more particularly not more than 5 wt % at 25° C. Any excess of halosilane of the general formula (3) that is present is preferably removed by distillation ahead of the aqueous workup. The aqueous workup before the removal of the siloxane of the general formula (1) of the invention is unfavorable, however, when the siloxane of the general formula (1) carries particularly moisture-sensitive radicals, such as halogen radicals or alkoxy radicals, for example, or has a high solubility in water. In that case, preference is given to removing the alkali metal salts by filtration and subsequent distillation or crystallization. It may be unnecessary to carry out purification if the purity of the filtrate is sufficient for the use of the siloxane of the general formula (1) of the invention, or if the secondary products have no adverse effect on the use of the reaction mixture.

The distillation of the target product from the optionally filtered reaction mixture or from the nonaqueous phase and, optionally, from the extract of the aqueous workup may preferably be carried out from the reaction vessel directly in a short path or a conventional distillation apparatus such as, for example, a rectifying column equipped with bubble trays, fixed-valve trays, or random or structured packing, or in a falling-film or thin-film evaporator, and also in a short-path distillation unit, batchwise or (semi)continuously. It is also possible for different distillation apparatuses to be utilized in succession; for example, large amounts of low boilers such as excess halosilane or solvents can be removed from the reaction vessel by distillation, after which the residue can be subjected to fractional purification in a distillation apparatus. The crystallization or an optional sublimation of the siloxane of the general formula (1) of the invention represents another possibility for isolation or purification.

In view of the sensitivity of halosilanes to hydrolysis, the reaction of the siliconate A with halosilane of the general formula (3) is preferably carried out in the absence of moisture, i.e., in a dried atmosphere or under reduced pressure, more preferably under inert gas such as nitrogen, $CO_2$, argon or lean air, preferably at 900 to 1100 hPa.

Preferably the following siloxanes of the general formula (1) are prepared by the process of the invention: [Vi-Si(OSiMe$_3$)O]$_4$, [Me-Si(OSiMe$_3$)O]$_4$, [Ph-Si(OSiMe$_3$)O]$_4$, [Ph-Si(OSiMe$_2$Ph)O]$_4$, [Ph-Si(OSiMe$_3$)O]$_3$, [Ph-Si(OSiMe$_2$Ph)O]$_3$, [Vi-Si(OSiMe$_2$H)O]$_4$, [Me-Si(OSiMe$_2$H)O]$_4$, Ph-Si(OSiMe$_2$H)O]$_4$, [Ph-Si(OSiMe$_2$H)O]$_3$, [Vi-Si(OSiMe$_2$Vi)O]$_4$, [Me-Si(OSiMe$_2$Vi)O]$_4$, [Ph-Si(OSiMe$_2$Vi)O]$_4$, [Ph-Si(OSiMe$_2$Vi)O]$_3$, [Vi-Si(OSiMe$_2$Cl)O]$_4$, [Me-Si(OSiMe$_2$Cl)O]$_4$, and [Ph-Si(OSiMe$_2$Cl)O]$_4$.

All of the above symbols in the above formulae have their definitions in each case independently of one another. In all formulae, the silicon atom is tetravalent.

In the inventive and comparative examples below, unless specified otherwise in each case, all quantity figures and percentage figures are by weight, and all reactions are carried out at a pressure of 1000 hPa (abs.).

The solids content is determined in each case using the HR73 Halogen Moisture Analyzer from Mettler Toledo at 160° C.

Example Series 1: Shows the Relation Between Alkali Metal/Si Ratio in the Siliconate A to the Proportion of Cyclic Siloxanes Formed (Target Product not Isolated)

a) Preparation of Siliconate Powders

First of all, in accordance with preparation example 1 in WO2012/022544 (PCT/EP2011/061766), siliconate powders are prepared from methyltrimethoxysilane, different proportions of KOH and/or NaOH, and water. The solids content in each case was at least 99.5%.

b) Reaction with Chlorosilane 10 ml of Isopar E (isoparaffinic hydrocarbon mixture with a boiling range of 113-143° C., available commercially from ExxonMobil) are admixed at 20° C. with 4 g (0.04 mol) of triethylamine (Aldrich), followed by cautious addition of 1 g in each case of finely pulverized siliconate powder (0.008-0.0096 mol, according to K/Na content). Over the course of 10 minutes and with stirring, 4 g (0.036 mol) of trimethylchlorosilane are metered in. The mixture increases in temperature and a white precipitate is formed. Stirring is carried out at 20° C. for 6 hours, 7 g (0.388 mol) of water are added, and stirring is continued vigorously for 30 minutes. The ammonium chloride precipitate is dissolved; undissolved constituents are removed by filtration and weighed; the composition of the upper, organic phase of the clear, two-phase mixture is determined by means of $^{29}$Si-NMR. The results are compiled in table 1.

TABLE 1

| Example | 1.1 *) | 1.2 | 1.3 | 1.4 | 1.5 | 1.6 [1)] | 1.7 |
|---|---|---|---|---|---|---|---|
| Alkali metal/Si (molar ratios) | 1.05 K | 0.75 K | 0.65 K | 0.65 K/Na 0.9/0.1 | 0.65 K/Na 0.7/0.3 | 0.65 K/Na 0.6/0.4 | 0.65 K/Na 0.5/0.5 |

TABLE 1-continued

| Example | 1.1 *) | 1.2 | 1.3 | 1.4 | 1.5 | 1.6 [1] | 1.7 |
|---|---|---|---|---|---|---|---|
| [2] (MT)$_4$ | 0 | 57.3 | 62 | 69 | 82 | 78 | 74 |
| [3] (M$_2$T)$_2$ | 83 | 32 | 34 | 24 | 11.5 | 2.9 | 3.8 |
| [4] Insoluble fraction | 8 | 13 | 17 | 17 | 12 | 11 | 14 |

*) not inventive
[1] siliconate powder used from example 7 in WO2012/022544
[2] molar fraction of [MeSi(OSiMe$_3$)O]$_4$ among the MeSiO$_{3/2}$-containing silicon compounds according to $^{29}$Si-NMR of (peaks at +8.4 ppm, –67 ppm)
[3] molar fraction of [MeSi(OSiMe$_3$)$_2$O$_{1/2}$]$_2$ among the MeSiO$_{3/2}$-containing silicon compounds according to $^{29}$Si-NMR (peaks at +7.3 ppm, –66.1 ppm)
[4] wt % relative to initial mass of siliconate powder From this it can be seen that the proportion of the cyclic target product in the reaction mixture increases as the alkali metal content goes down, and that a defined sodium fraction raises the selectivity.

Example 2: [MeSi(OSiMe$_2$Vi)O]$_4$

A 0.5 l, 5-neck flask rendered inert using nitrogen and equipped with paddle stirrer, thermometer, solids lock, and 20 cm Vigreux column with top-mounted column attachment (condenser) is charged with 181 g (1.5 mol) of vinyldimethylchlorosilane (WACKER CHEMIE AG). Via the solids lock, with stirring, 56.5 g (0.5 mol, 0.325 mol potassium) of SILRES BS Powder S (WACKER CHEMIE AG, potassium methylsiliconate powder with a K:Si molar ratio of 0.65) are metered in at a rate such that the temperature of the reaction mixture does not exceed 25° C. (~3:45 h). The reaction mixture is subsequently heated at reflux until evolution of gas can no longer be determined (~1 h). With stirring, 160 g of fully demineralized water are added. The bottom phase is drained off and the upper phase is fractionally distilled under reduced pressure. The target product passes into the receiver at a boiling range of 120-128° C. and 2 hPa.

The product isolated is 31.2 g of a clear, colorless liquid (=40% of theory) which according to $^1$H- and $^{29}$Si-NMR and also GC-MS is an isomer mixture of cyclosiloxane [MeSi(OSiMe$_2$Vi)O]$_4$ with a purity of 98.5%.

Example 3: [MeSi(OSiMe$_2$H)O]$_4$

A 0.5 l, 5-neck flask rendered inert using nitrogen and equipped with paddle stirrer, thermometer, solids lock, and 20 cm Vigreux column with top-mounted column attachment (condenser) is charged with 113.1 g (1.19 mol) of dimethylchlorosilane (WACKER CHEMIE AG). Via the solids lock, with stirring, 45 g (0.4 mol, 0.26 mol potassium) of SILRES BS Powder S (WACKER CHEMIE AG, potassium methylsiliconate powder with a K:Si molar ratio of 0.65) are metered in at a rate such that the temperature of the reaction mixture does not exceed 25° C. (~2 h). The reaction mixture is subsequently heated at reflux until evolution of gas can no longer be determined (~1 h). With stirring, 68 g of fully demineralized water are added. The bottom phase is drained off and the upper phase is fractionally distilled under reduced pressure. The target product goes over into the receiver at a boiling range of 100-105° C. and 2 hPa.

The product isolated is 34.1 g of a clear, colorless liquid (=64% of theory) which according to $^1$H- and $^{29}$Si-NMR and also GC-MS is an isomer mixture of cyclosiloxane [MeSi(OSiMe$_2$H)O]$_4$ with a purity of 98%.

Example 4: [ViSi(OSiMe$_2$H)O]$_4$ a) Preparation of Potassium Vinyl-Siliconate (K:Si=0.65)

A 2 l 4-neck flask rendered inert with nitrogen and equipped with paddle stirrer, thermometer, two dropping funnels, and water separator with top-mounted column attachment (condenser) is charged with stirring and in parallel from the two dropping funnels with 422 g (2.83 mol) of vinyltrimethoxysilane (Geniosil® XL 10 from WACKER CHEMIE AG) and 282 g of 36.6% strength potassium hydroxide solution (1.84 mol of KOH) over the course of 10 minutes, with the apparatus having been conditioned to 22° C. The heat of reaction released causes the mixture to undergo an increase in temperature. The clear reaction mixture is heated at reflux for 30 minutes (around 72° C.), after which 142.9 g of distillate are taken off. Then 800 g of Isopar E (isoparaffinic hydrocarbon mixture having a boiling range of 113-143° C., available commercially from Exxon-Mobil) are added. The mixture is heated under reflux on a water separator. The distillate separates out as the bottom phase in the water separator. Up to a boiling temperature of 118° C., 228.8 g of clear, colorless distillate are collected, and are united with the first distillate. Analysis of the combined distillates by gas chromatography gives a methanol content of 73.2%, a water content of 26.6%, and an Isopar E content of 0.2%. The hydrolysis of the methoxy radicals in the vinyltrimethoxysilane is therefore quantitative. During the distillation, a pastelike white solid separates out in the reaction mixture, and breaks down increasingly into fine particles, forming a suspension. After azeotropic drying, the solvent is removed by distillation at 120° C. and the solid residue is dried for an hour at 120° C. and 10 hPa. This gives 326.5 g of fine, white, free-flowing powder with a solids content of 99.5% (determined using the HR73 Halogen Moisture Analyzer from Mettler Toledo at 160° C.). From this it is possible to compute an average molar mass for the potassium vinylsiliconate of 115 g/mol.

b) Preparation of the Siloxane [ViSi(OSiM$_2$H)O]$_4$

A 0.5 l, 5-neck flask rendered inert using nitrogen and equipped with paddle stirrer, thermometer, solids lock, and 20 cm Vigreux column with top-mounted column attachment (condenser) is charged with 114.6 g (1.2 mol) of dimethylchlorosilane (WACKER CHEMIE AG) at −15° C. Via the solids lock, with stirring, 50 g (0.43 mol, 0.28 mol potassium) of the potassium vinyl-siliconate from a) are metered in at a rate such that the temperature of the reaction mixture does not exceed 25° C. (45 minutes). The reaction mixture is subsequently heated at reflux until evolution of gas can no longer be determined (~1 h). With stirring, a solution of 37.5 g of ethanol in 112.5 g of fully demineralized water is added. The bottom phase is drained off and the upper phase is fractionally distilled under reduced pressure. The target product passes into the receiver at a boiling range of 135-137° C. and 4 hPa.

The product isolated is 21.6 g of a clear, colorless liquid (=34% of theory) which according to $^2$H- and $^{29}$Si-NMR is an isomer mixture of cyclosiloxane [vinylSi(OSiMe$_2$H)O]$_4$ with a purity of 94%.

Example 5: [ViSi(OSiMe$_2$Vi)O]$_4$

A 0.5 l, 5-neck flask rendered inert using nitrogen and equipped with paddle stirrer, thermometer, solids lock, and 20 cm Vigreux column with top-mounted column attachment (condenser) is charged with 147.6 g (1.2 mol) of vinyldimethylchlorosilane (WACKER CHEMIE AG) at 20° C. Via the solids lock, with stirring, 50 g (0.43 mol, 0.28 mol potassium) of the potassium vinyl-siliconate from example 4a) are metered in at a rate such that the temperature of the reaction mixture does not exceed 25° C. (85 minutes). The reaction mixture is subsequently heated at reflux until evolution of gas can no longer be determined (~1 h). With stirring, a solution of 20 g of ethanol in 150 g of fully demineralized water is added. The bottom phase is drained off and the upper phase is fractionally distilled under reduced pressure. The target product passes into the receiver at a boiling range of 120-166° C. and 4 hPa.

The product isolated is 20.3 g of a clear, colorless liquid (=28% of theory) which according to $^2$H- and $^{29}$Si-NMR is an isomer mixture of cyclosiloxane [vinylSi(OSiMe$_2$vinyl)O]$_4$ with a purity of 93%.

Example 6: [ViSi(OSiMe$_3$)O]$_4$

A 0.5 l, 5-neck flask rendered inert using nitrogen and equipped with paddle stirrer, thermometer, solids lock, and 20 cm Vigreux column with top-mounted column attachment (condenser) is charged with 132.9 g (1.2 mol) of trimethylchlorosilane (WACKER CHEMIE AG) at 21° C. Via the solids lock, with stirring, 50 g (0.43 mol, 0.28 mol potassium) of the potassium vinyl-siliconate from example 4a) are metered in at a rate such that the temperature of the reaction mixture does not exceed 25° C. (120 minutes). The reaction mixture is subsequently heated at reflux until evolution of gas can no longer be determined (~1 h). With stirring, a solution of 50 g of ethanol in 150 g of fully demineralized water is added. The bottom phase is drained off and the upper phase is fractionally distilled under reduced pressure. The target product passes into the receiver at a boiling range of 120-130° C. and 5 hPa.

The product isolated is 24.8 g of a clear, colorless liquid (=37% of theory) which according to $^2$H- and $^{29}$Si-NMR is an isomer mixture of cyclosiloxane [vinylSi(OSiMe$_3$)O]$_4$ with a purity of 97%.

Comparative Example C1 a) Preparation of Potassium Vinyl-Siliconate (K:Si=1)

In a procedure analogous to that of example 4a), 300 g (2 mol) of vinyltrimethoxysilane (Geniosil® XL 10 from WACKER CHEMIE AG) are reacted with 251.4 g of 45% strength potassium hydroxide solution (2 mol of KOH). The clear reaction mixture is subsequently dried azeotropically with 1200 g of Isopar E (isoparaffinic hydrocarbon mixture with a boiling range of 113-143° C., available commercially from ExxonMobil). This gives 260 g of fine, white, free-flowing powder with a solids content of 98.5% (determined using the HR73 Halogen Moisture Analyzer from Mettler Toledo at 160° C.). From this it is possible to compute an average molar mass for the potassium vinylsiliconate of 128 g/mol.

b) Reaction of Potassium Vinylsiliconate 6a) with Trimethylchlorosilane

A 0.5 l, 5-neck flask rendered inert using nitrogen and equipped with paddle stirrer, thermometer, solids lock, and 20 cm Vigreux column with top-mounted column attachment (condenser) is charged with 156.4 g (1.44 mol) of trimethylchlorosilane (WACKER CHEMIE AG) at 22° C. Via the solids lock, with stirring, 50 g (0.39 mol, 0.39 mol potassium) of the potassium vinyl-siliconate from comparative example C1a) are metered in at a rate such that the temperature of the reaction mixture does not exceed 25° C. (120 minutes). The reaction mixture is subsequently heated at reflux until evolution of gas can no longer be determined (~1 h). With stirring, a solution of 125 g of ethanol in 125 g of fully demineralized water is added. To improve phase separation, 13.3 g of sodium chloride are added. The aqueous, bottom phase is drained off. In the attempt to distill the upper, organic phase under reduced pressure, a solid residue is formed which cannot be distilled and which has a melting point>300° C.

The invention claimed is:
1. A process for preparing cyclic siloxanes of the formula (1)

$$[RSi(OSiR^1R^2R^3)O]_n \qquad (1),$$

comprising:
reacting alkali metal salts of silanols of the formula (2), $$R—Si(OH)_{3-m}(OM)_m \qquad (2),$$

wherein m is 0, 1, 2, or 3, and over all species of the alkali metal salts of silanols of the formula (2), m is on average 0.1 to <1,
their hydrolysis/condensation products, or alkali metal salts of silanols of the formula (2) together with their hydrolysis/condensation products, wherein the molar ratio of cation M to silicon is <1,
with halosilanes of the formula (3)

$$R^1R^2R^3Si\text{-Hal} \qquad (3)$$

where
n is 3, 4, 5, 6, 7 or 8,
R is an organic radical bonded via carbon to silicon,
M is an alkali metal cation,
Hal is a halogen radical, and
$R^1$, $R^2$, and $R^3$ are hydrogen, $C_{1-10}$ alkoxy radicals, $C_{1-20}$ aryloxy radicals or monovalent hydrocarbon radicals having 1 to 18 carbon atoms which are unsubstituted or substituted by halogen atoms or alkoxy groups,
and thereby producing cyclic siloxanes of the formula (1).
2. The process of claim 1, wherein R is a monovalent, Si—C-bonded hydrocarbon radical having 1 to 30 carbon atoms, which is unsubstituted or substituted by halogen atoms, $C_{1-6}$ alkyl or $C_{1-6}$ alkoxy groups or silyl groups, and in which one or more mutually nonadjacent —CH$_2$— units are optionally replaced by —O— or —S—.
3. The process of claim 1, wherein M comprises sodium, potassium, or a mixture thereof.
4. The process of claim 2, wherein M comprises sodium, potassium, or a mixture thereof.
5. The process of claim 1, wherein the molar ratio M:Si in formula (2) is from 0.4 to 0.85.
6. The process of claim 2, wherein the molar ratio M:Si in formula (2) is from 0.4 to 0.85.
7. The process of claim 3, wherein the molar ratio M:Si in formula (2) is from 0.4 to 0.85.
8. The process of claim 1, wherein the halosilanes of formula (3) are chlorosilanes.
9. The process of claim 2, wherein the halosilanes of formula (3) are chlorosilanes.
10. The process of claim 3, wherein the halosilanes of formula (3) are chlorosilanes.
11. The process of claim 5, wherein the halosilanes of formula (3) are chlorosilanes.
12. The process of claim 1, wherein reacting is carried out at 0° C. to 120° C.
13. The process of claim 2, wherein reacting is carried out at 0° C. to 120° C.
14. The process of claim 3, wherein reacting is carried out at 0° C. to 120° C.

15. The process of claim 5, wherein reacting is carried out at 0° C. to 120° C.

16. The process of claim 8, wherein reacting is carried out at 0° C. to 120° C.

17. The process of claim 1, wherein reacting is carried out without auxiliary base.

18. The process of claim 2, wherein reacting is carried out without auxiliary base.

19. The process of claim 3, wherein reacting is carried out without auxiliary base.

20. The process of claim 5, wherein reacting is carried out without auxiliary base.

21. The process of claim 1, wherein n is 4.

* * * * *